United States Patent
Fischbach et al.

(10) Patent No.: US 11,679,183 B2
(45) Date of Patent: Jun. 20, 2023

(54) MEDICAL CONTACT SHOCK FREEZER

(71) Applicant: B MEDICAL SYSTEMS S.A.R.L., Hosingen (LU)

(72) Inventors: Jos Fischbach, Hosingen (LU); Alan Rushing, Hosingen (LU)

(73) Assignee: B. MEDICAL SYSTEMS S.A.R.L., Hosingen (LU)

( * ) Notice: Subject to any disclaimer, the term of this patent is extended or adjusted under 35 U.S.C. 154(b) by 0 days.

(21) Appl. No.: 17/848,578

(22) Filed: Jun. 24, 2022

(65) Prior Publication Data
US 2022/0323655 A1  Oct. 13, 2022

Related U.S. Application Data

(63) Continuation of application No. 16/618,189, filed as application No. PCT/EP2018/063409 on May 22, 2018, now Pat. No. 11,612,679.

(51) Int. Cl.
*A61M 1/02* (2006.01)
*F25D 31/00* (2006.01)

(52) U.S. Cl.
CPC ......... *A61M 1/0272* (2013.01); *F25D 31/001* (2013.01); *F25D 2331/8014* (2013.01)

(58) Field of Classification Search
CPC ................ A61M 1/0272; F25D 31/001; F25D 2331/8014; F25D 2400/30; F25D 2331/801
See application file for complete search history.

(56) References Cited

U.S. PATENT DOCUMENTS

| | | | |
|---|---|---|---|
| 2,254,406 A | 9/1941 | Zarotschenzeff | |
| 2,910,837 A | 11/1959 | Patterson | |
| 2,927,443 A * | 3/1960 | Knowles | F25D 31/001 |
| | | | 62/341 |
| 2002/0195234 A1* | 12/2002 | Wu | F28F 3/12 |
| | | | 165/144 |
| 2012/0305570 A1 | 12/2012 | Aprea et al. | |

FOREIGN PATENT DOCUMENTS

| | | | | |
|---|---|---|---|---|
| BE | 1015127 A | 10/2004 | | |
| CN | 203848601 U | 9/2014 | | |
| CN | 104075539 A | 10/2014 | | |
| CN | 104374164 * | 2/2015 | | |
| CN | 104374164 A * | 2/2015 | | |
| CN | 104374164 A | 2/2015 | | |
| CN | 105920689 A | 7/2016 | | |
| DE | 4324192 A1 | 1/1995 | | |
| DE | 102007052014 A1 * | 5/2009 | ........... | F25D 31/001 |
| DE | 102007052014 A1 | 5/2009 | | |
| EP | 1134000 A | 9/2001 | | |
| EP | 1524481 A1 | 4/2005 | | |
| EP | 1596899 B1 | 4/2010 | | |
| SU | 1794236 C | 2/1993 | | |
| WO | 200014463 A1 | 3/2000 | | |
| WO | WO-0014463 A1 * | 3/2000 | ........... | F25D 31/001 |

* cited by examiner

*Primary Examiner* — Frantz F Jules
*Assistant Examiner* — Martha Tadesse
(74) *Attorney, Agent, or Firm* — Jerold Schneider; Schneider IP Law

(57) ABSTRACT

A medical contact shock freezer adapted for fast freezing a plurality of individual bags containing a medical liquid has the contact surface of its upper freezing plate arranged at an angle of at least 2° to the horizontal.

15 Claims, 3 Drawing Sheets

MEDICAL CONTACT SHOCK FREEZER

CROSS-REFERENCE TO RELATED APPLICATIONS

This application is a continuation of pending U.S. application Ser. No. 16/616,189 filed on Nov. 29, 2019, as the U.S. National Stage Entry of PCT Application No. PCT/EP2018/063409 filed May 22, 2018, claiming priority to United Kingdom Application No. 170881504 filed on Jun. 2, 2017, the entireties of each of which is hereby incorporated by reference.

BACKGROUND OF THE INVENTION

This invention relates to a medical contact shock freezer adapted for fast freezing a plurality of individual bags containing a medical liquid, for example blood plasma, a biological preparation or a pharmaceutical preparation, and to a method of freezing medical liquids.

A known medical contact shock freezer is described in EP1596899, the contents of which are hereby incorporated by reference. Appropriate features described in EP1596899 may be used in relation to the present invention.

Blood plasma bags are commonly used to store, transport and dispense blood plasma and comprise flexible plastics walls which may be made of polyethylene, polypropylene or plasticized PVC. In order to ensure plasma quality, once the plasma has been obtained, for example by plasmapheresis, it is desirable for the plasma contained within a filled, sealed plasma bag to be completely frozen to a temperature of −30° C. or less within a short time period. The step of rapidly freezing the plasma, for example from its collection temperature or from room temperature to −30° C., is facilitated by use of a contact shock freezer in which a plurality of plasma bags are pressed between cooling plates which are chilled by a circulating coolant. Once frozen, the plasma bags are transferred to a medical storage freezer which may be maintained at a temperature of −30° C., −50° C. or below.

SUMMARY OF THE INVENTION

In accordance with one of its aspects, the present invention provides a medical contact shock freezer in accordance with claim 1. Other aspects are defined in independent claims. The dependent claims define preferred or alternative features.

It has surprising been found that the reliability of and/or time required for freezing a plurality of individual bags in a medical shock freezer can be improved by arranging the contact surface of the upper freezing plate at an angle to the horizontal and/or angling the bags containing the medical liquid. Whilst not wishing to be bound by theory, it is believed that although bags containing blood plasma are intended to be sealed without the presence of any air in the bag, even when following good practice, it is possible for at least some plasma bags within a plurality of bags being prepared together to contain some air. When the plasma bags are loaded into a shock freezer having horizontal cooling plates such that the plasma bags are horizontal, any plasma bag containing air will have an air pocket formed between the plasma and its upper plastics wall and positioned towards the centre of the upper wall of the bag. Despite the pressure applied to the plasma bags by the cooling plates, it is believed that such an air bubble significantly reduces the transfer of heat from the plasma to the cooling plates and thus slows down freezing of the plasma in any bag in which such an air bubble is present. It has surprisingly been found that by angling the bags and/or the upper and/or lower freezing plate, any air bubbles present are displaced away from the centre of the plasma bag and are less disruptive to the desired freezing cycle. The ability to automatically compensate for even occasional and undesired presence of an air bubble in one or more bag being frozen is particularly significant for medical liquids in respect of which it is important to ensure that each bag being frozen is frozen to a desired temperature in a desired time. The invention may thus be used, for example, to improve reliability of the process of freezing a medical liquid and/or reduce the necessity of relying upon, for example, an increase in freezing time or a reduction in the temperature of the freezing plates to ensure conformity.

Each bag to be frozen may contain a quantity of medical liquid, notably plasma, which is ≥150 ml, ≥200 ml or ≥250 ml and/or ≤1000 ml, ≤850 ml, ≤500 ml or ≤450 ml or ≤350 ml. Each bag may have a nominal volume of 500 ml; in this case, each bag may contain about 250 ml of medical liquid, notably plasma, for example from a whole blood donation of 500 ml. Each bag may have a nominal volume of 1000 ml; in this case, each bag may contain about 850 ml of medical liquid, notably plasma, for example from plasmapheresis.

The or each pair of freezing plates may define an operating surface, that is to say a surface at which individual bags can be arranged for freezing, which has an area ≥0.25 m², ≥0.3 m², ≥0.4 m², ≥0.5 m², ≥0.55 m², ≥0.7 m² or ≥0.8 m² and/or ≤1.4 m², ≤1.3 m²≤1.2 m² or ≤1 m². For example, the or each pair of freezing plates may define an operating surface which has:

a width that is ≥0.4 m, ≥0.5, ≥0.6 m, ≥0.7 m, ≥0.8 m or ≥0.9 m and/or ≤1.6 m, ≤1.5 m, ≤1.2 m or less than 1.1 m; and/or a depth that is ≥0.5 m, ≥0.6 m and/or ≤1.1 m, ≤1 m or ≤0.9 m.

Such dimensions facilitate loading of the bags by an operator. The or each pair of freezing plates may be configured and/or dimensioned to simultaneously freeze ≥9 bags, ≥12 bags, ≥16 bags, ≥21 bags or ≥30 bags and/or ≤50, ≤48, ≤40 or ≤32 bags, notably 500 ml nominal volume bags. For example, the or each pair of freezing plates may be configured and/or dimensioned to simultaneously freeze 3, 4, 5, 6, 7 8 or 9 rows of bags arranged across its width with 3 or 4 bags in each row arranged along its depth, notably bags having a nominal volume of 500 ml. Particularly in the case of bags containing between 150 ml and 355 ml of medical liquid to be frozen, individual bags may be stacked one on another to form i) a first layer of bags, each bag in the first layer having a lower side which is in contact with the contact surface of a lower freezing plate of a pair of freezing plates and ii) a second layer of bags, each bag in the second layer having a lower side which sits on an upper side of a bag in the first layer of bags and an upper side which, in the freezing position, is in contact with the contact surface of an upper freezing plate of the pair of freezing plates. Preferably, each bag has an outlet from which the medical liquid will be extracted, and the outlet is arranged facing the rear of the shock freezer.

Each freezing plate may be configured to operate at a temperature which is ≤−40° C., ≤−45° C. or ≤−50° C. This provides rapid shock freezing. This operating temperature is preferably reached with 30 minutes, within 25 minutes or within 20 minutes of initial operation of the shock freezer. The freeze time required to attain a core temperature of the medical liquid in the bags of −30° C. is preferably ≤60 minutes, ≤50 minutes or more preferably ≤45 minutes, notably when the or each pair of freezing plates are fully loaded with bags to be frozen at an initial temperature of 20° C., notably bags each containing ≥200 ml or ≤250 ml and/or ≤1000 ml or ≤850 ml of blood plasma. Preferably, such a freezing performance is achieved with an initial temperature which is ≥25° C., ≥30° C. or ≥32° C. and/or ≤35° C.

It has been found that an improvement in the freezing cycle can be obtained with a fairly small angle of the upper and/or lower contact surfaces of the freezing plate, for example an angle of about 2° to the horizontal. An angle of between 3° and 10°, notably 5°, to the horizontal provides an advantageous effect combined with a configuration which facilitates loading and unloading of the bags. Nevertheless, the angle may be increased and may be ≥about 2° and/or ≤about 30°, ≤about 20° or ≤about 15°. At higher angles it is advantageous to configure the contact surface of the lower freezing plate to reduce the chance of the bags slipping along the inclined surface. The contact surface(s) of the freezing plate(s) preferably incline such that it rear portion is higher that its front portion; this facilitates loading and unloading of the plasma bags. Alternatively, the contact surface(s) of the freezing plate(s) may be inclined such that its rear portion is lower that its front portion.

Clamping of the individual bags between the contact surface of the upper and lower freezing plates is preferably affected in such a way that the surfaces of the bags in contact with the freezing plates are flattened; this increases the contact area and improves heat transfer. Sufficient force may be applied to clamp the bags between the freezing plates such that a pressure which is ≥0.1 bar or ≥0.2 bar and/or ≤0.5 bar is generated in the medical liquid within the bag.

The movement of the upper and/or lower freezing plate from the loading position to the freezing position is preferably a linear movement, notably a vertical linear movement, without rotation of the plate. This facilitates accurate clamping of the plurality of bags between the plates. Preferably, the contact surfaces of upper and lower freezing plates of a pair of freezing plates are parallel in their freezing position and remain parallel during movement between the loading and the freezing position. This further facilitates accurate clamping of the plurality of bags. The use of parallel and preferably planer contact surfaces of upper and lower freezing plates of a pair of freezing plates is also advantageous when it is desired for the shock freezer to be useable in a configuration having two layers the bags arranged between a pair of freezing plates. Preferably, the angle of each freezing plate to the horizontal is fixed, that is to say this angle does not change; each freezing plate may be fixed in rotation so that it cannot rotate. At least one of the upper and lower freezing plates of a pair of freezing plates may be associated with a linear drive to affect its movement from the loading to the freezing position, for example one or more pneumatic or hydraulic cylinders, notably a pair of spaced cylinders, for example arranged at opposite sides of the freezing plate. The movement may be guided by a linear guide arrangement, for example comprising a linear guide arranged at each of the left and right sides of the freezing plate. Each linear guide may comprise a pair of, preferably vertical, tubular guide elements which together guide the movement.

Preferably, one of the upper and lower freezing plates of a pair of freezing plates is fixed and does not move; this provides a mechanically advantageous arrangement. An arrangement in which the shock freezer comprises:

a first pair of upper and lower freezing plates and a second pair of upper and lower freezing plates, the first pair being arranged above the second pair;

in which the first pair of upper and lower freezing plates comprises an immobile lower freezing plate and a moveable upper freezing plate; and in which the second pair of upper and lower freezing plates comprises an immobile upper freezing plate and a moveable lower freezing plate;

and notably in which the lower freezing plate of the first pair of freezing plates and the upper freezing plate of the second pair of freezing plates are provided by a single, integrated freezing plate, provides a compact and convenient arrangement for providing two pairs of freezing plates to enable simultaneous freezing of a large number of individual bags whilst minimising the footprint of the shock freezer and facilitating loading and unloading.

Arranging the contact surfaces of the upper and lower freezing plates as planar contact surfaces, preferably parallel, planar contact surfaces, facilitates use of the shock freezer with bags of different sizes and allows for use of mechanically simple clamping of the bags.

The shock freezer is provided with suitable cooling apparatus to cool the freezing plates to their desired temperature, for example a cooling fluid provided in a cooling circuit comprising a compressor, a condenser, and an evaporator. Preferably, the cooling apparatus is arranged within the footprint of the cooling plates. The power rating of the shock freezer may be ≥1.5 kW, ≥2 kW, ≥2.5 kW or ≥4 kW and/or ≤0 kW or ≤8 kW.

BRIEF DESCRIPTION OF THE DRAWINGS

An embodiment of the invention will now be described, by way of example only, with reference to the accompanying drawings, of which.

DETAILED DESCRIPTION

Figure 1:
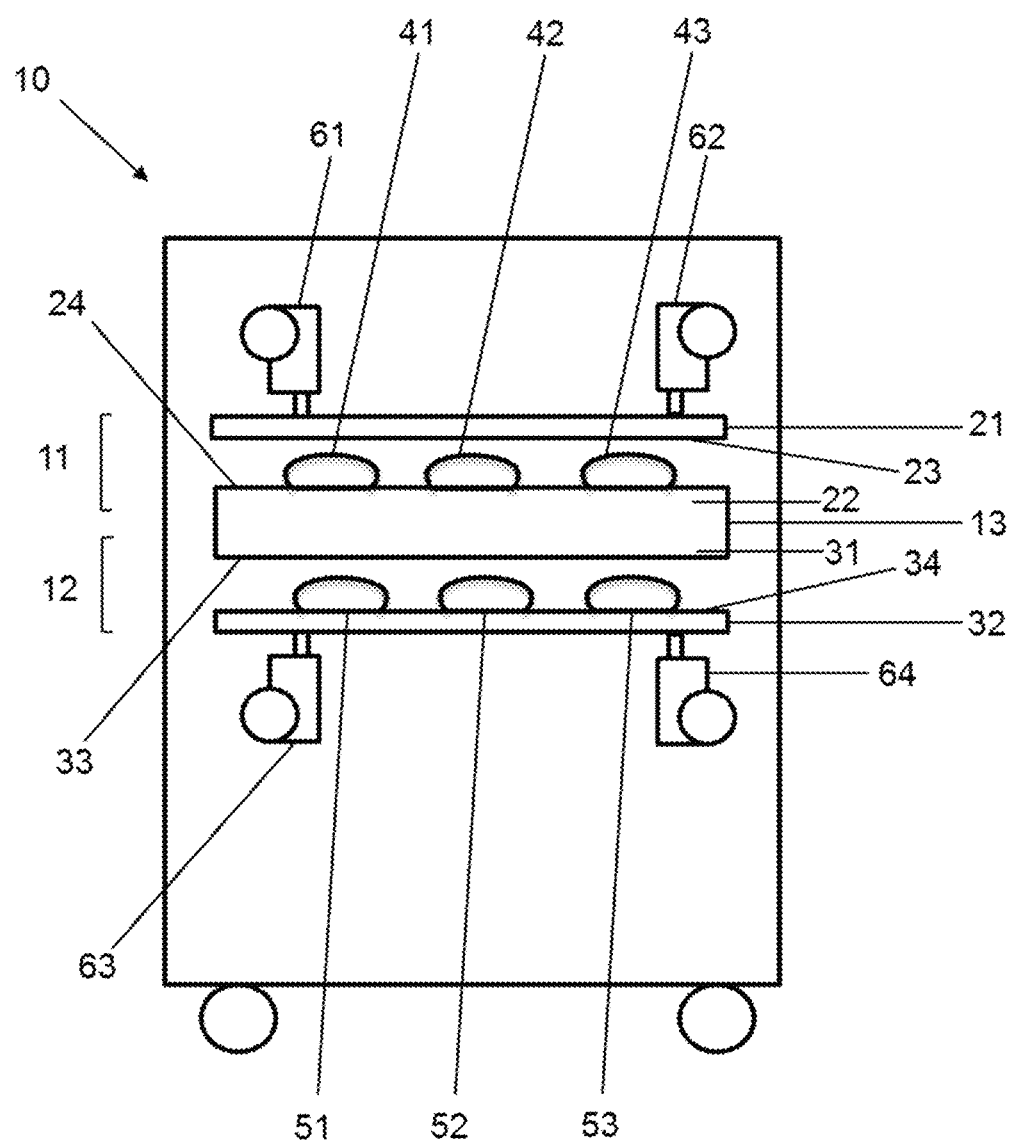
FIG. 1 is schematic front view of a shock freezer with its freezing plates in their loading position.

The illustrated contact shock freezer 10 comprises: a first pair 11 of upper 21 and lower 22 freezing plates; and a second pair 12 of upper 31 and lower 32 freezing plates; the first pair 11 being arranged above the second pair 12. The lower freezing plate 22 of the first pair of freezing plates 11 and the upper freezing plate 31 of the second pair of freezing plates 12 are provided by a single, immobile, integrated freezing plate 13.

In use, with each pair 11, 12 of freezing plates in its loading position (FIG. 1), a first series of plasma bags to be frozen is arranged in rows (the front bag 41, 42, 43 of each row being illustrated in FIG. 1) between the upper 21 and lower 22 freezing plates of the first pair of freezing plates 11 by being placed on an operating surface provided by the lower freezing plate 22 by an operator standing in front of the freezer 10. A second series of plasma bags to be frozen is similarly arranged in rows (the front bag 51, 52, 53 of each row being illustrated in FIG. 1) between the upper 31 and lower 32 freezing plates of the second pair of freezing plates 12 by being placed on an operating surface provided the lower freezing plate 32 by an operator standing in front of the freezer 10. Each pair 11, 12 of freezing plates is then moved from its loading position (FIG. 1) to its freezing position (FIG. 2) in the following way: the upper freezing plate 21 of the first pair of freezing plates 11 is moved vertically downwards by a pair of vertically arranged hydraulic cylinders 61, 62 arranged at the left side 61 and right side 62 of the upper freezing plate to clamp the first series of plasma bags to be frozen between a contact surface 23 of the upper freezing plate 21 and a contact surface 24 of the lower freezing plate 22; and the lower freezing plate 32 of the second pair 12 of freezing plates is moved vertically upwards by a pair of vertically arranged hydraulic cylinders 63, 64 arranged at the left side 63 and right side 64 of the lower freezing plate 32 to clamp the second series of plasma bags to be frozen between a contact surface 33 of the upper freezing plate 31 and a contact surface 34 of the lower freezing plate 32. In the freezing position (FIG. 2), with the plasma bags 41, 42, 43, 51, 52, 53 clamped between their respective freezing plates, the plasma in the bags is frozen from a temperature of about 20° C. to a temperature of −30° C. in a time of about 40 minutes. Once the plasma bags have been frozen, each pair of freezing plates 11, 12 is moved from its freezing position (FIG. 2) to its loading position (FIG. 1) and the plasma bags are removed by an operator standing at the front of the shock freezer 10 and placed in cold storage.

Figure 2:
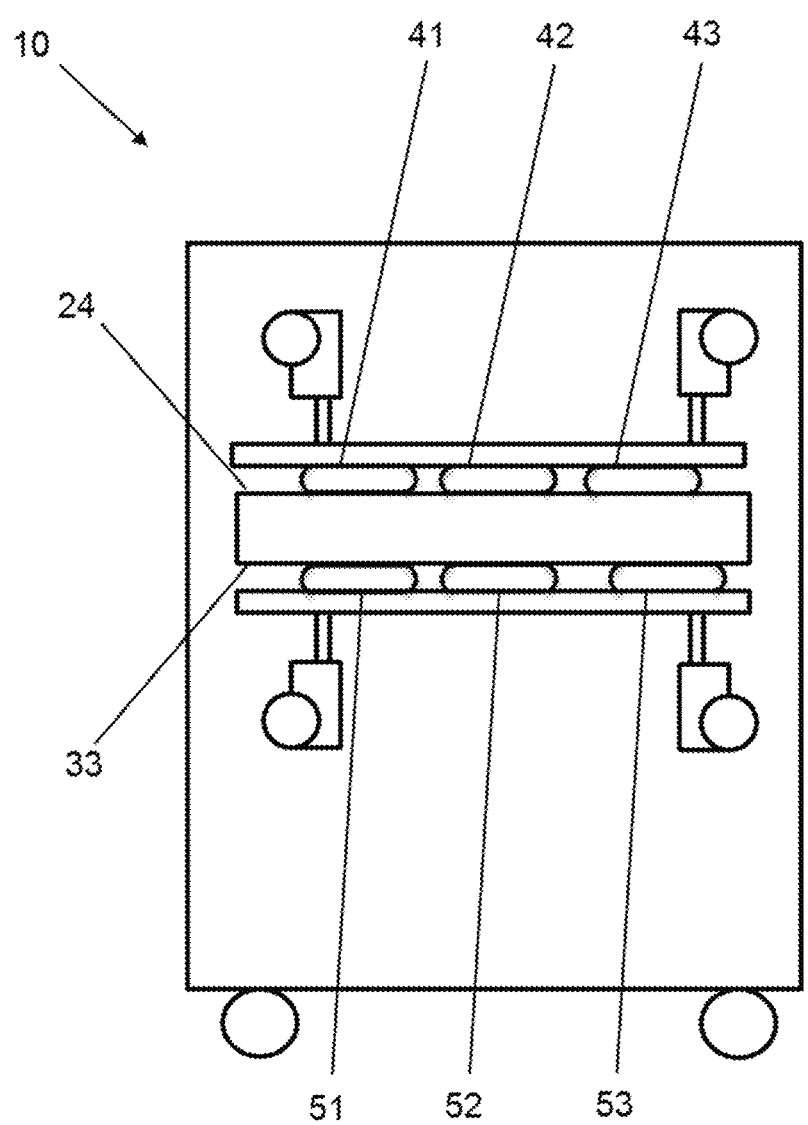
FIG. 2 is a schematic front view of the shock freezer with its freezing plates in their freezing position.
Figure 3:
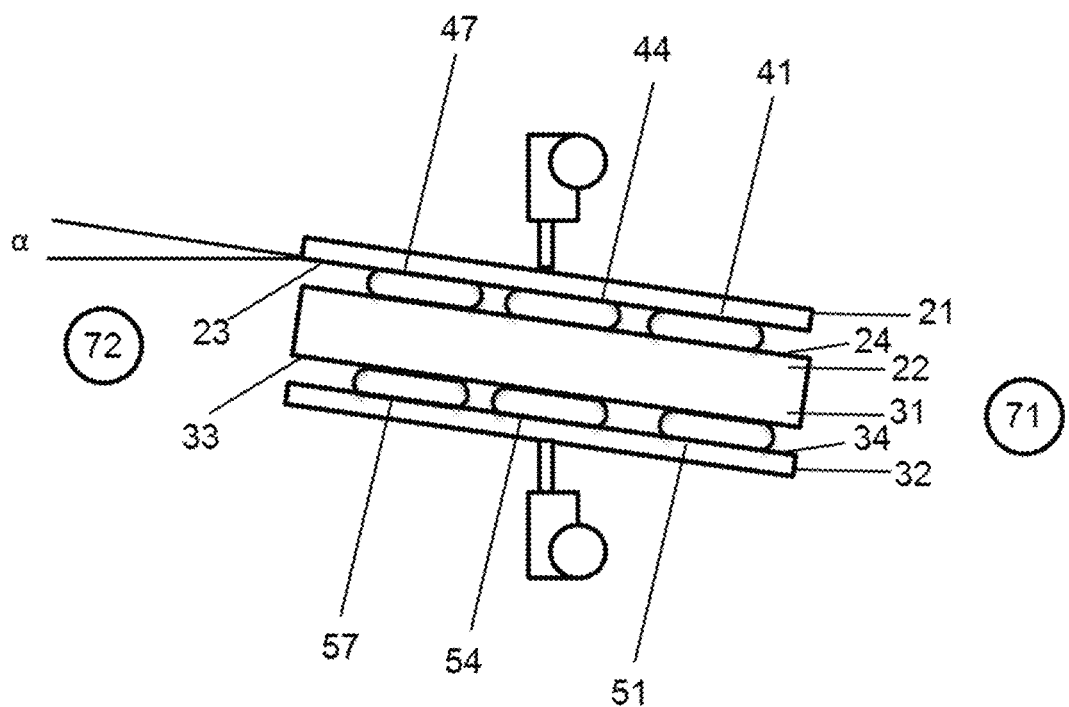
FIG. 3 is a schematic side view of the freezing plates in their freezing position.

The illustrated contact shock freezer 10 is shown schematically with nine plasma bags arranged between each pair 11, 12 of freezing plates. The first pair 11 of freezing plates 11 has three lines of plasma bags arranged across its width (of which the front bag 41, 42, 43 of each line is illustrated in FIG. 1 and FIG. 2) and three lines of plasma bags arranged across its depth (of which the left side bag 41, 44, 47 of each row is illustrated in FIG. 3). The illustrated arrangement for the second pair 12 of freezing plates is similar. Flattening and compression of the plasma bags in the freezing position is schematically illustrated in FIG. 2.

Contact surfaces 23, 24 of the first pair 11 of freezing plates 21, 22 are each planar and parallel to each other and are arranged to slope upwardly from the front 71 to the rear 72 of the shock freezer 10 at an angle α to the horizontal. Similarly, contact surfaces 33, 34 of the second pair 12 of freezing plates 31, 32 are each planar and parallel to each other and are arranged to slope upwardly from the front 71 to the rear 72 of the shock freezer 10 at an angle α to the horizontal. The angle α is preferably between about 2° and about 10°, for example about 5° but has been shown in an exaggerated fashion in FIG. 3 for illustrative purposes.

As shown in FIG. 3, each bag is held in an angled bag configuration at an angle α to the horizontal, that is to say, a plane passing centrally through each bag with respect to its upper and lower walls has an angle α to the horizontal.

The invention claimed is:

1. A medical contact shock freezer adapted for fast freezing a plurality of individual bags containing a medical liquid, the individual bags being arranged side by side, adjacent to each other,
in which the contact shock freezer comprises a pair of freezing plates configured to operate at a temperature which is equal to or less than −40° C., the pair of freezing plates comprising an upper freezing plate and a lower freezing plate;
in which one of the upper and lower freezing plates of the pair of freezing plates is a fixed freezing plate which is fixed and does not move;
in which another one of the upper and lower freezing plates of the pair of freezing plates is a moveable freezing plate which is moveable to define
i) a loading position in which sufficient separation is provided between the freezing plates to load or unload the individual bags between the freezing plates and
ii) a freezing position in which each individual bag is in contact with and is clamped between a contact surface of the upper freezing plate and a contact surface of the lower freezing plate in such a way that surfaces of the individual bags containing the medical liquid that are in contact with the freezing plates are flattened so as to increase a contact area and improve heat transfer; in which the contact surfaces of the upper and lower freezing plates of the pair of freezing plates are parallel in their freezing position and remain parallel during movement between the loading and the freezing position;
in which, in the freezing position, the contact surface of the upper freezing plate is arranged at an angle which is ≥2° and ≤30° with respect to the horizontal;
wherein movement between the loading and freezing position of the pair of freezing plates consists of a linear, vertical displacement of the movable freezing plate.

2. The medical contact shock freezer of claim 1, in which the shock freezer comprises a first pair of the upper and lower freezing plates and a second pair of the upper and lower freezing plates, the first pair of upper and lower freezing plates being arranged above the second pair of upper and lower freezing plates;
in which the first pair of upper and lower freezing plates comprises an immobile lower freezing plate and a moveable upper freezing plate;
in which the second pair of upper and lower freezing plates comprises an immobile upper freezing plate and a moveable lower freezing plate; and
in which, in the freezing position, the contact surface of each of the upper freezing plates is arranged at an angle which is 2° and 30° with respect to the horizontal.

3. The medical contact shock freezer of claim 2, in which the lower freezing plate of the first pair of freezing plates and the upper freezing plate of the second pair of upper and lower freezing plates are provided by a single, integrated freezing plate.

4. The medical contact shock freezer of claim 1, in which in the freezing position, the contact surface of the upper freezing plate is arranged at an angle of between 3° and 10° to the horizontal.

5. The medical contact shock freezer of claim 1, in which the contact surface of the upper freezing plate and the contact surface of the lower freezing plate are each planar contact surfaces.

6. The medical contact shock freezer of claim 1, in which the pair of freezing plates defines an operating surface which has:
a width that is ≥0.4 m and ≤1.6 m; and
a depth that is ≥0.5 m and ≤1.1 m.

7. The medical contact shock freezer of claim 1, in which each freezing plate is configured to operate at a temperature which is ≤−50° C.

8. The medical contact shock freezer of claim 1, in which, in the freezing position, the contact surface of the upper freezing plate and the contact surface of the lower freezing plate are each arranged at an angle of about 5° to the horizontal.

9. A method of shock freezing a plurality of individual bags containing a medical liquid, wherein the method comprises: arranging the individual bags side by side, adjacent to each other between the upper freezing plate and the lower freezing plate of t the contact shock freezer of claim 1 with the plates arranged in a bag loading position;

subsequently closing the freezing plates to the freezing position by moving the moveable freezing plate to clamp each individual bag of the plurality of individual bags in contact with the contact surface of the upper freezing plate and the contact surface of the lower freezing plate with each of the individual bag of the plurality of individual bags being held in an angled bag configuration at an angle which is ≥2° and ≤30° with respect to the horizontal, and in which closing the freezing plates to the freezing position by moving the moveable freezing plate to clamp each of the individual bag of the plurality of individual bags in contact with the contact surface of the upper freezing plate and the contact surface of the lower freezing plate consists of displacing the moveable freezing plate linearly and vertically;

subsequently freezing the medical liquid in each of the individual bag of the plurality of individual bags to a temperature of −20° C. or below through heat exchange between the medical liquid and the upper and lower freezing plates; subsequently moving the moveable freezing plate to the loading position and removing frozen bags from the shock freezer.

10. The method of claim 9, in which each of the individual bag of the plurality of individual bags is held in then angled bag configuration at an angle of between 3° and 10° to the horizontal.

11. The method of claim 10, in which each of the individual bag of the plurality of individual bags is held in the angled bag configuration due to angling of the contact surfaces of the upper and lower freezing plates.

12. The method of claim 9, in which each bag holds the medical liquid selected from blood plasma, a biological preparation and a pharmaceutical preparation.

13. The method of claim 9, in which freezing the medical liquid in each of the individual bag of the plurality of individual bags comprises freezing each of the individual bag from a temperature of between 15° C. and 25° C. to a temperature of −25° C. or below.

14. The method of claim 13, in which the freezing is accomplished in a freezing time of 60 minutes or less.

15. The method of claim 9, in which the individual bags are selected from i) bags containing between about 150 ml and 450 ml of blood plasma and ii) bags containing between about 750 ml and 950 ml of blood plasma.

* * * * *